(12) United States Patent
Wendland et al.

(10) Patent No.: US 11,147,911 B2
(45) Date of Patent: Oct. 19, 2021

(54) AUTO-INJECTOR STORAGE DEVICE

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 16/609,959

(22) PCT Filed: May 2, 2018

(86) PCT No.: PCT/EP2018/061119
§ 371 (c)(1),
(2) Date: Oct. 31, 2019

(87) PCT Pub. No.: WO2018/202667
PCT Pub. Date: Nov. 8, 2018

(65) Prior Publication Data
US 2020/0054821 A1   Feb. 20, 2020

(30) Foreign Application Priority Data

May 3, 2017 (EP) .................................... 17169262

(51) Int. Cl.
*A61M 5/00* (2006.01)

(52) U.S. Cl.
CPC ..... *A61M 5/002* (2013.01); *A61M 2205/3368* (2013.01)

(58) Field of Classification Search
CPC ...................... A61M 5/002; A61M 2205/3368
See application file for complete search history.

(56) References Cited

U.S. PATENT DOCUMENTS

| 5,245,117 A | * | 9/1993 | Withers | A61M 5/3205 206/366 |
| 6,302,855 B1 | * | 10/2001 | Lav | A61B 5/150412 600/584 |
| 7,240,806 B2 | * | 7/2007 | Choi | B65D 83/02 221/212 |
| 7,815,046 B2 | * | 10/2010 | Sansoucy | A61M 5/002 206/366 |
| 8,945,066 B2 | * | 2/2015 | Bochenko | A61M 5/31 604/189 |
| 9,555,191 B2 | * | 1/2017 | Edwards | A61M 5/2053 |

(Continued)

FOREIGN PATENT DOCUMENTS

| CN | 101076312 | 11/2007 |
| CN | 101102947 | 1/2008 |

(Continued)

OTHER PUBLICATIONS

International Preliminary Report on Patentability in Application No. PCT/EP2018/061119, dated Nov. 5, 2019, 6 pages.

(Continued)

*Primary Examiner* — Michael Collins
(74) *Attorney, Agent, or Firm* — Fish & Richardson P.C.

(57) ABSTRACT

A storage device for storing a plurality of auto-injectors, the device configured to activate an auto-injector upon removal of the auto-injector from the device.

20 Claims, 7 Drawing Sheets

(56) References Cited

U.S. PATENT DOCUMENTS

| | | | |
|---|---|---|---|
| 9,861,768 B2* | 1/2018 | Kataoka | A61M 5/3287 |
| 10,318,714 B2* | 6/2019 | Portnoy | G06F 19/3468 |
| 2002/0050462 A1* | 5/2002 | Penney | B65D 85/20 |
| | | | 206/363 |
| 2004/0182736 A1* | 9/2004 | Mesa | B32B 27/32 |
| | | | 206/521 |
| 2005/0009391 A1 | 1/2005 | Jordan et al. | |
| 2006/0069345 A1 | 3/2006 | Anderson et al. | |
| 2008/0083769 A1 | 4/2008 | Yuyama et al. | |
| 2009/0114667 A1 | 5/2009 | Sansoucy et al. | |
| 2009/0128330 A1* | 5/2009 | Monroe | A61B 90/98 |
| | | | 340/568.1 |
| 2010/0185178 A1 | 7/2010 | Sharp et al. | |
| 2011/0168733 A1 | 7/2011 | Yuyama et al. | |
| 2012/0179112 A1* | 7/2012 | Langley | A61M 5/14566 |
| | | | 604/228 |
| 2013/0245604 A1* | 9/2013 | Kouyoumjian | A61M 5/1408 |
| | | | 604/506 |
| 2014/0048555 A1* | 2/2014 | Dasbach | A61M 5/002 |
| | | | 221/101 |
| 2015/0105903 A1* | 4/2015 | Denny | A61J 7/0076 |
| | | | 700/237 |
| 2015/0165121 A1* | 6/2015 | Murakami | A61M 5/20 |
| | | | 604/154 |
| 2015/0251839 A1* | 9/2015 | Denny | B65D 83/02 |
| | | | 340/686.6 |
| 2015/0283332 A1* | 10/2015 | Woehr | A61M 5/3202 |
| | | | 604/192 |
| 2015/0366882 A1 | 12/2015 | Altschul et al. | |
| 2017/0143893 A1 | 5/2017 | Hasumi et al. | |
| 2018/0085515 A1* | 3/2018 | Mide | B65D 75/326 |

FOREIGN PATENT DOCUMENTS

| | | |
|---|---|---|
| CN | 102159172 | 8/2011 |
| CN | 104955435 | 9/2015 |
| DE | 212015000190 | 3/2017 |
| EP | 2357013 | 8/2011 |
| WO | WO 03/077973 | 9/2003 |
| WO | WO 2012/177948 | 12/2012 |
| WO | WO 2014/089083 | 6/2014 |

OTHER PUBLICATIONS

International Search Report and Written Opinion in Application No. PCT/EP2018/061119, dated Aug. 6, 2018, 5 pages.

* cited by examiner

AUTO-INJECTOR STORAGE DEVICE

CROSS-REFERENCE TO RELATED APPLICATIONS

The present application is the national stage entry of International Patent Application No. PCT/EP2018/061119, filed on May 2, 2018, and claims priority to Application No. EP 17169262.7, filed on May 3, 2017, the disclosures of which are incorporated herein reference.

TECHNICAL FIELD

The present disclosure relates to a device for storing a plurality of auto-injectors.

BACKGROUND

Current therapies delivered by means of self-administered injections include drugs for diabetes (both insulin and new GLP-A class drugs), migraine, hormone therapies, anticoagulants etc. Drug delivery devices such as auto-injectors are devices which completely or partially replace activities involved in medicament delivery of manual devices.

SUMMARY

According to an aspect of the present disclosure, there is provided a storage device for storing a plurality of auto-injectors, the device configured to activate an auto-injector upon removal of the auto-injector from the device. This allows the auto-injector to be maintained in a storage state up until the moment it is ready for use by an end user, wherein correct activation of the auto-injector can be ensured, with minimal effort on the part of the user. This is particularly appropriate where the end user has little or no medical experience.

The device may be configured to activate the auto-injector by at least partially opening a blister pack containing the auto-injector. The auto-injector may therefore be kept sterile until the moment it is ready for use by an end user.

The device may be configured to activate the auto-injector by modifying the auto-injector. This interaction of the device with the auto-injector provides a simple means of activating an auto-injector with minimal input required from a user.

The device may be configured to activate the auto-injector by breaking or completing an electrical circuit of the auto-injector. The auto-injector may be kept in a low-power dormant state until the moment it is ready for use by an end user, thus conserving power.

The device may be configured to activate the auto-injector by detaching a part of the auto-injector. This is a simple means of activating an auto-injector with minimal input required from a user.

The device may comprise a connector coupled to the auto-injector and a surface of the device, wherein the connector is configured to decouple from the auto-injector to activate the auto-injector. This is a particularly simple means of activating the auto-injector.

The device may comprise a blister pack configured to contain the auto-injector, wherein the connector is coupled to the blister pack and the auto-injector and is configured to decouple from the auto-injector to activate the auto-injector. This is a particularly simple means of activating the auto-injector by an end user.

The device may comprise a box configured to contain the auto-injector, wherein the device comprises a dispenser arranged to dispense an auto-injector contained within the box, and wherein the dispenser is configured to inhibit removal of two or more auto-injectors from the device simultaneously. This arrangement can prevent accidental or intentional activation of more than one auto-injector, thus encouraging use of a first auto-injector before a second auto-injector is removed.

The dispenser may comprise a drawer moveable between an open position and a closed position, wherein an auto-injector can be removed from the device via the drawer when in the open position. This is a particularly simple means of allowing an auto-injector to be removed.

The device may be configured to inhibit subsequent storage of the auto-injector in the device after the auto-injector has been previously removed from the device and activated. By preventing storage of a previously-activated auto-injector, it can be ensured that each auto-injector removed from the device is newly activated and hence in good condition for use.

The device may be configured to activate the auto-injector by changing a geometry of the auto-injector from a first state to a second state, wherein the device is configured to store the auto-injector when in the first state and is further configured to inhibit storage of the auto-injector in the device when the auto-injector is in the second state. This is a particularly simple and effective means of preventing storage of a previously-activated auto-injector.

The device may comprise a control unit; a sensor coupled to the control unit; and an actuator coupled to the control unit, wherein the control unit is configured to: determine whether an auto-injector has been activated based upon a signal from the sensor; and in response to determining that the auto-injector has been activated, send a signal to the actuator to move it from a first position, in which the auto-injector can be stored in the device, to a second position, in which the auto-injector is inhibited from being stored in the device. This is a particularly simple and effective means of preventing storage of a previously-activated auto-injector.

According to another aspect of the present disclosure, there is provided a system comprising any aforementioned device and the plurality of auto-injectors, wherein the auto-injectors contain a medicament. This allows the auto-injector to be maintained in a storage state up until the moment it is ready for use by an end user, wherein correct activation of the auto-injector can be ensured, with minimal effort on the part of the user. This is particularly appropriate where the end user has little or no medical experience.

The system may further comprise an activation indicator, wherein the activation indicator is configured to indicate to a user that the auto-injector is activated. This can improve user confidence that an auto-injector has been successfully activated, and can deter the user from attempting to store the activated auto-injector back in the device.

The system may comprise a temperature indicator configured to indicate a temperature of the auto-injector to a user, wherein the temperature indicator is activated upon removal of the auto-injector from the device. The auto-injector can be stored at the correct temperature up until the moment it is required for use, with the user being made aware that the auto-injector is at the correct temperature for injection by the temperature indicator.

BRIEF DESCRIPTION OF THE FIGURES

Exemplary embodiments of the present disclosure are described with reference to the accompanying drawings, in which.

Reference will now be made in detail to examples illustrated in the accompanying drawings, wherein like reference numerals refer to like elements throughout.

DETAILED DESCRIPTION

A storage device for storing a plurality of auto-injectors and a system comprising the storage device and the plurality of auto-injectors are provided. The storage device is configured to (automatically) activate at least one of the auto-injectors in response to removal of the auto-injector from the device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include an auto-injector. The device can include a cartridge-based system that requires piercing a sealed ampule before use. Volumes of medicament delivered with these devices can range from about 0.5 ml to about 2 ml.

In combination with a specific medicament, the drug delivery devices may also be customized in order to operate within required specifications. For example, the device may be customized to inject a medicament within a certain time period (e.g., about 3 to about 20 seconds for auto-injectors). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be triggered via a trigger mechanism. Such a trigger mechanism can include one or more of a button, a lever, a needle sleeve, or other trigger component. Triggering of an automated function may be a one-step or multi-step process. That is, a user may need to trigger one or more trigger components in order to cause the automated function. For example, in a one-step process, a user may depress a needle sleeve against their body in order to cause injection of a medicament. Other devices may require a multi-step triggering of an automated function. For example, a user may be required to depress a button and retract a needle shield in order to cause injection.

In addition, triggering of one automated function may trigger one or more subsequent automated functions, thereby forming a trigger sequence. For example, triggering of a first automated function may trigger at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
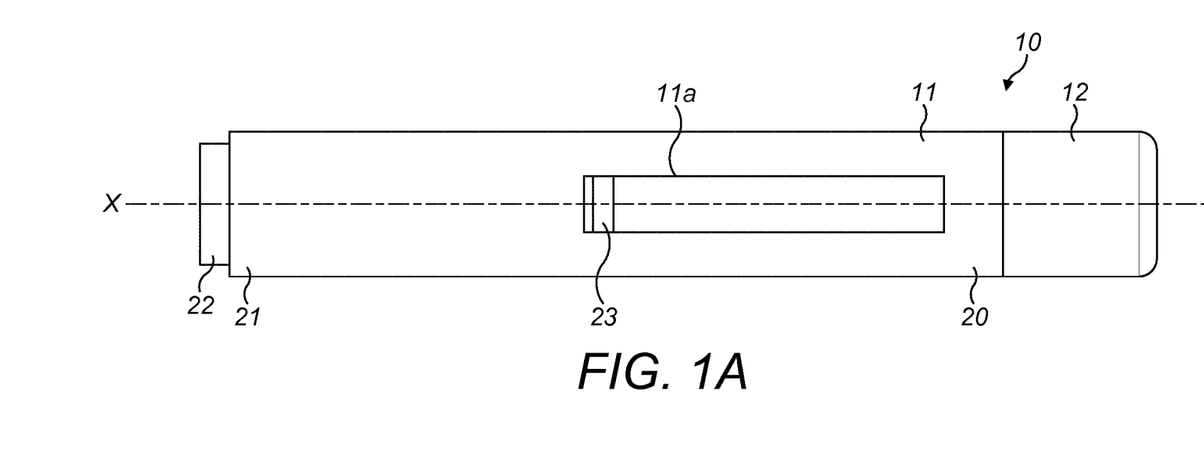
FIGS. 1A and 1B are side-on views of an auto-injector.
Figure 1B:
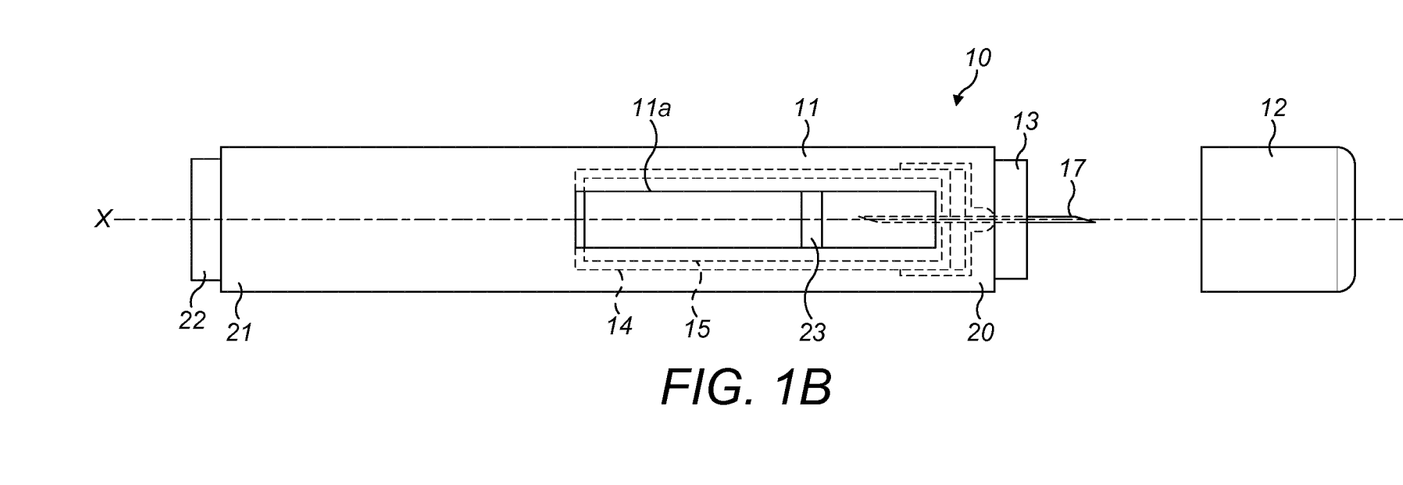

An example auto-injector 10 is shown in FIGS. 1A & 1B. Auto-injector 10, as described above, is configured to inject a medicament into a patient's body. Auto-injector 10 includes a housing 11 which typically contains a reservoir containing the medicament to be injected (e.g., a syringe) and the components required to facilitate one or more steps of the delivery process. Auto-injector 10 can also include a cap assembly 12 that can be detachably mounted to the housing 11. Typically a user must remove cap 12 from housing 11 before auto-injector 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Auto-injector 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of trigger mechanism, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before auto-injector 10 is triggered. A proximal end of the drive spring can be fixed within proximal region 21 of housing 11, and a distal end of the drive spring can be configured to apply a compressive force to a proximal surface of piston 23. Following triggering, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes auto-injector 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of auto-injector 10 can be locked as required.

Auto-injectors, such as auto-injector 10, may need to be activated before they are ready to be used for an injection. In this context, activating auto-injector 10 can mean changing a state of auto-injector 10 from a storage state to an intermediary state. For example, in a storage state auto-injector 10 can be configured to not allow triggering of the auto-injector 10. As explained below, this can include safety tabs or other structural features that preclude or limit device triggering. In contrast, an intermediary state can allow triggering of the device. For example, following removal of a safety tab auto-injector 10 can be used for an injection. As described below, activating auto-injector 10 can use mechanical or electrical components.

If the auto-injector 10 comprises electronic circuitry used for performing an injection process then activating the auto-injector 10 may comprise placing the circuitry in a condition to allow for an injection to take place. The circuitry may be in a dormant state, such that activation of the auto-injector 10 awakens the circuitry from the dormant state.

In other examples, activating the auto-injector 10 may comprise a physical activation of the auto-injector 10 such as movement of a mechanical feature of the auto-injector 10 in preparation for an injection. For example, activation may comprise removing or unlocking a safety catch on the auto-injector, or opening a valve to allow a plurality of medicaments to mix prior to injection.

According to some embodiments, the auto-injector storage device 100 is configured to activate an auto-injector 10 by breaking or completing an electrical circuit 30 of the auto-injector 10.

Figure 2A:
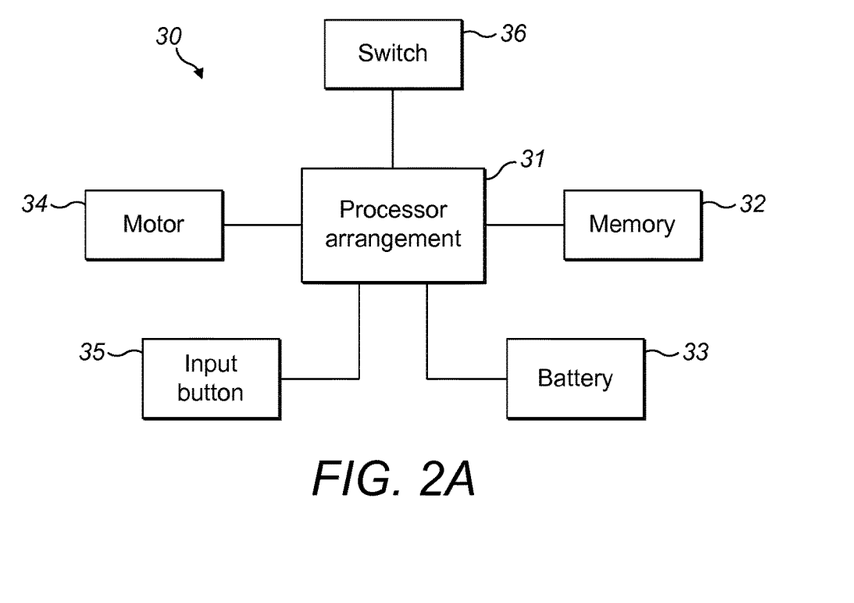
FIG. 2A is a schematic diagram of circuit within the auto-injection device of FIGS. 1A and 1B.

FIG. 2A is a schematic diagram of an electrical circuit 30 contained within an auto-injector 10. The circuit 30 comprises a processor arrangement 31 and memory 32 which work together to control the operation of one or more features of the auto-injector 10. The circuit 30 also comprises a battery 33 or other power source for supplying power to the processor arrangement 31 and other components of the circuit 30. The circuit 30 may further comprise a motor 34 for driving one or more mechanisms of the auto-injector 10. The circuit 30 may also comprise an input button 35. The input button 35 may be actuated by a user of the auto-injector 10 to provide an input to the circuit 30, which may cause the processor arrangement 31 to control operation of a function of the auto-injector 10. For example, actuation of the input button 35 may initiate delivery of medicament from the syringe of the auto-injector 10.

The auto-injector storage device 100 may be configured to activate an auto-injector 10 containing a circuit 30 by breaking at least part of the circuit 30. In other words, the device 100 may be configured to break an electrical connection of the circuit 30. This electrical connection may be provided by a switch 36 forming part of the circuit 30. In response to the auto-injector 10 being removed from the storage device 100, switch 36 may be moved from a closed position to an open position thereby breaking part of circuit 30. This opening of the switch 36 may be sensed by processor arrangement 31, causing the auto-injector 10 to be activated.

Figure 2B:
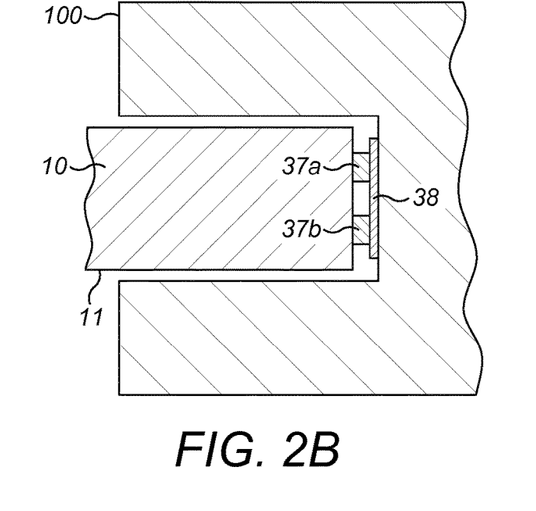
FIG. 2B is a partial cross-sectional view of an auto-injector storage device and auto-injector.

FIG. 2B is a cross-sectional view of part of an auto-injector storage device 100 and the end of an auto-injector 10. The auto-injector 10 comprises two electrical contacts 37a and 37b, here arranged on a surface of the housing 11 of the auto-injector 10. The auto-injector storage device 100 comprises an electrical connector 38 arranged on a surface of the device 100. When the auto-injector 10 is stored in the device 100, the connector 38 makes contact with the two electrical contacts 37a and 37b, thereby forming an electrical connection between the contacts 37a and 37b. Upon removal of the auto-injector 10 from the device 100, electrical contact between the two electrical contacts 37a and 37b via the connector 38 is broken. This is sensed by processing arrangement 31 of circuit 30 connected to the two electrical contacts 37a and 37b, resulting in activation of the auto-injector 10.

The auto-injector storage device 100 may be configured to activate an auto-injector 10 containing circuit 30 by completing at least part of the circuit 30. In other words, the device 100 may be configured to form an electrical connection between two parts of the circuit 30. This electrical connection may again be provided by a switch 36 forming part of the circuit 30. In response to the auto-injector 10 being removed from the storage device 100, switch 36 may be moved from an open position to a closed position thereby breaking part of circuit 30. This opening of the switch 36 may be sensed by processor arrangement 31, causing the auto-injector 10 to be activated.

Figure 2C:
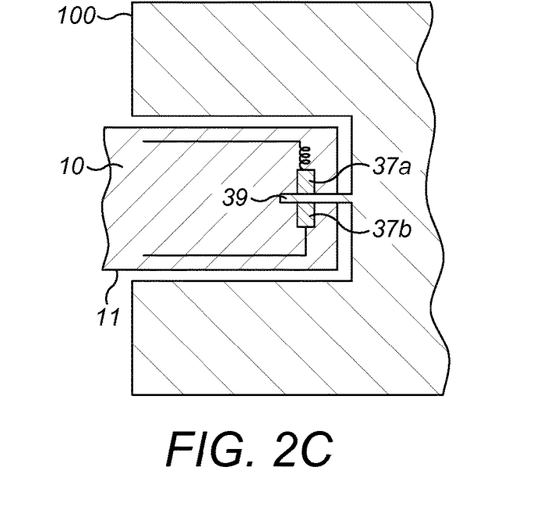
FIG. 2C is a partial cross-sectional view of an auto-injector storage device and auto-injector.

FIG. 2C is a cross-sectional view of part of an auto-injector storage device 100 and the end of an auto-injector 10. The auto-injector 10 comprises two electrical contacts 37a and 37b, contained within housing 11 of the auto-injector 10, however they may also be located elsewhere in relation to the housing 11, for example on an external surface of the housing 11. The auto-injector storage device 100 comprises a protrusion 39 arranged on a surface of the device 100. When the auto-injector 10 is stored in the device 100, the protrusion 39 holds the two electrical contacts 37a and 37b apart, thereby breaking any electrical connection between the contacts 37a and 37b. Upon removal of the auto-injector 10 from the device 100, the protrusion 39 is removed from between the two electrical contacts 37a and 37b. The two electrical contacts 37a and 37b are biased towards each other, for example by a spring, such that they make electrical contact once the protrusion 39 has been removed. Removal of the protrusion 39 therefore results in completion of electrical circuit 30. Completion of electrical contact between the two electrical contacts 37a and 37b may be sensed by processing arrangement 31 of circuit 30 connected to the two or more electrical contacts 37a and 37b, resulting in activation of the auto-injector 10.

The two electrical contacts 37a and 37b of FIGS. 2B and 2C form part of circuit 30. Breaking of the circuit 30 as shown in FIG. 2B may be sensed by the processor arrangement 31. In response, the processor arrangement 31 activates the auto-injector 10. In this context, activation of the auto-injector 10 may comprise enabling one or electrical functions of the circuit 30, such as enabling use of input button 35 or motor 34.

Completion of the circuit 30 as shown in FIG. 2C may be sensed by the processor arrangement 31. In response, the processor arrangement 31 activates the auto-injector 10. In this context, activation of the auto-injector 10 may comprise enabling one or electrical functions of the circuit 30, such as enabling use of input button 35 or motor 34. In some embodiments, completion of the circuit 30 may comprise completion of an electrical connection between battery 33 and one or more components of circuit 30, such as processor arrangement 31. In other words, circuit 30 may initially have no power supply. However, following the completion of an electrical circuit in response to removal of the auto-injector 10 from the device 100, power may be supplied to the circuit 30 from the battery 33.

In some embodiments, the device 100 is configured to activate the auto-injector 10 by modifying the auto-injector 10 as the auto-injector 10 is removed from the device 100. In other words, removal of an auto-injector 10 from the device 100 may result in (physical) modification of the auto-injector 10 by the device 100. The modification may be permanent or temporary.

The device 100 may be configured to activate the auto-injector 10 by mechanically (or physically) modifying the auto-injector 10 as the auto-injector 10 is removed from the device 100. As an example, removal of an auto-injector 10 from the device 100 may result in the device 100 mechanically moving part of the auto-injector 10 from a first position, wherein the auto-injector 10 is deactivated, to a second position, wherein the auto-injector 10 is activated. The part may be a valve of the auto-injector 10, wherein the valve is moved from a first position to a second position, wherein the auto-injector 10 is activated when the valve is in the second position. In another example, the part may be a safety catch, wherein the safety catch is moved from a first position, in which the auto-injector 10 is not ready for use, to a second position, in which the auto-injector 10 is activated and ready for use.

In some examples, the device 100 may be configured such that the mechanical modification of the auto-injector 10 is carried out by the user as they remove the auto-injector 10 from the device 100. For example, the device 100 may be configured to store the auto-injector 10 such that a user must mechanically modify an auto-injector 10 in order to remove it from the device 100. This may involve storing an auto-injector 10 such that a user must actuate an activation button located on the auto-injector as they remove the auto-injector from the device 100. Pressing the activation button activates the auto-injector 10. In some examples, the activation button is actuated by the device 100 as the auto-injector 10 is removed.

In some examples, mechanically moving part of the auto-injector 10 from a first position to a second position may comprise detaching said part from the remainder of the auto-injector 10 by the device 100. For example the part may be a movement limiter which prevents some mechanical operation of the auto-injector 10, such as the depression of a button. Mechanically moving part of the auto-injector 10 from a first position to a second position may comprise detaching the movement limiter from the remainder of the auto-injector 10 by the device 100, thereby allowing the previously inhibited operation of the auto-injector 10. The part detached from the auto-injector 10 by the device 100 may be a cap 12 of the auto-injector 10, as discussed later.

The device 100 may be configured such that removal of an auto-injector 10 from the device 100 requires a specific operation or sequence of operations to be performed by a user on the auto-injector 10 and/or device 100. The operation or sequence of operations may comprise one or movements of at least part of the auto-injector 10 and/or device 100. The movements may include rotation or translation. The device 100 may comprise a restraining means configured to hold an auto-injector 10 and prevent its removal until the specific operation or sequence of operations is performed. The restraining means may comprise one or more recesses and/or protrusions arranged to engage with one or more corresponding recesses and/or protrusions located on the auto-injector 10, to prevent removal of the auto-injector 10 from the device 100 until the specific operation or sequence of operations is performed.

As an example, the sequence of operations may comprise both a linear translation and a rotational movement of the auto-injector 10, relative to the device 100, whereby a user must press down and twist an auto-injector 10 before removing it from the device 100. The requirement of a specific operation or sequence of operations to be performed can serve as a child-proof restriction on removal and activation of the device, whereby an auto-injector 10 can only be removed from the device 100, and hence be activated, by performance of the correct operation or sequence of operations.

The specific operation or sequence of operations may be performed by a user at least in part on the device 100. For example, the operation or sequence of operations may comprise a user squeezing the restraining means before an auto-injector 10 can be removed.

If a user is interrupted between removing an auto-injector 10 from the device 100 and performing an injection, they may attempt to put the activated auto-injector 10 back into storage in the device 100. However, where a plurality of auto-injectors 10 are stored in the device 100, there is a risk that the use forgets which auto-injector 10 has already been activated (and thus may have compromised sterility or a reduced battery life). Therefore in some embodiments of the present disclosure, the device 100 is configured to inhibit subsequent storage of the auto-injector 10 in the device 100 after the auto-injector 10 has been previously removed from the device 100 and activated. In some examples this may be achieved by mechanical modification of the auto-injector 10 as discussed previously.

The device 100 may be configured to activate the auto-injector 10 by changing geometry of the auto-injector 10 from a first state to a second state as the auto-injector 10 is removed from the device 100. The device 100 may be configured to store the auto-injector 10 when the auto-injector 10 is in the first state. The device 100 is further configured to inhibit storage of the auto-injector 10 in the device 100 when the auto-injector 10 is in the second state. For example, the device 100 may comprise an aperture that has a geometry that allows an auto-injector 10 to be received through the aperture and stored in the device 100 when the auto-injector 10 is in the first state, but the geometry of the aperture may prevent or inhibit auto-injector 10 to be received through the aperture and stored in the device 100 when the auto-injector 10 is in the second state.

Figure 3:
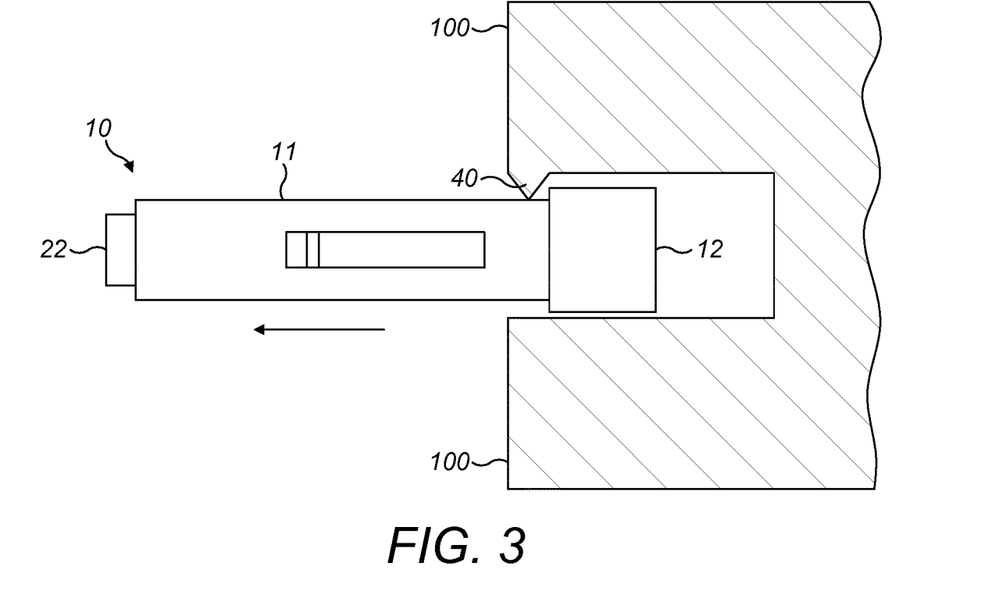
FIG. 3 is a cross-sectional view of an auto-injector storage device and auto-injector in accordance with an embodiment of the invention.

FIG. 3 is a cross-sectional view of an auto-injector storage device 100 and auto-injector 10. The auto-injector 10 comprises a cap 12. The device 100 of FIG. 3 is configured to activate the auto-injector 10 by detaching the cap 12 from the auto-injector 10. The cap 12 may be detached such that it cannot be attached again. The device 100 may comprise detachment means configured to detach the cap 12 from an auto-injector 10.

FIG. 3 shows the device 100 comprises a protrusion 40 acting as the detachment means, wherein the protrusion detaches the cap as the auto-injector 10 is removed from the device 100 in the direction of the arrow. However, it can be understood that other means of detaching the cap can be provided.

The device 100 may detach the cap 12 such that the cap 12 is fully removed from the remainder of the auto-injector 10 and remains within the device 100. However in other examples, the device 100 is configured to detach the cap 12, but the cap 12 remains with the remainder of the auto-injector 10. In other words, the cap 12 is loosened from the remainder of the auto-injector 10.

Detaching the cap may be the change in geometry of the auto-injector 10 discussed previously. That is, the first state of the auto-injector 10 is when the cap 12 is attached to the auto-injector 10, and the second state of the auto-injector 10 is when the cap 12 is detached from the auto-injector 10.

In some embodiments protrusion 40 is configured to activate the auto-injector 10 in another manner, for example by tearing packaging such as blister pack 50 containing the auto-injector 10. The protrusion 40 may be configured to tear the blister pack 50 as the auto-injector 10 is removed from the device 100. A user may subsequently remove the auto-injector 10 from the blister pack 50, prior to injection. Protrusion 40 may, for example, comprise a blade configured to tear the blister pack 50.

Figure 4:
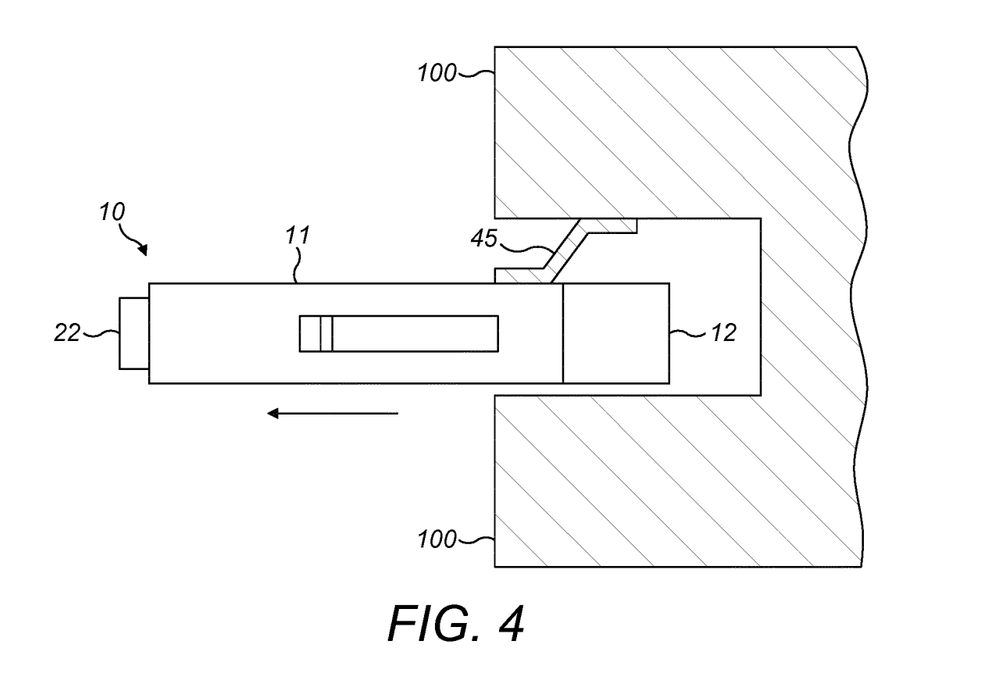
FIG. 4 is a cross-sectional view of an auto-injector storage device and auto-injector in accordance with an embodiment of the invention.

FIG. 4 is a cross-sectional view of an auto-injector storage device 100 and auto-injector 10. As can be seen from FIG. 4, the device 100 comprises a connector 45 coupled to the auto-injector 10 and to a surface of the device 100. The connector 45 may be a tab. The connector 45 is configured to decouple from the auto-injector 10 to activate the auto-injector 10 as the auto-injector 10 is removed from the device 100.

When the connector 45 is coupled to the auto-injector 10 and device 100, the auto-injector 10 is in a non-activated state. Removal of the auto-injector 10 from the device 100, for example by a user, causes the connector 45 to decouple (or detach) from the auto-injector 10.

In one example of a non-activated state, part of the connector 45 coupled to the auto-injector 10 may be covering button 22 of the auto-injector 10, preventing actuation of the button 22 by a user. Removal of the auto-injector 10 from the device 100 causes the connector 45 to decouple (or detach) from the auto-injector 10, uncovering the button 22 and allowing the user to actuate the button 22 and perform an injection. In another example, in a non-activated state of the auto-injector 10, the connector may be breaking or completing an electrical circuit 30 contained within the auto-injector 10, which is inhibiting use of the auto-injector 10. Removal of the auto-injector 10 from the device 100 causes the connector 45 to decouple (or detach) from the auto-injector 10, completing the circuit 30 if it was previously broken, or breaking the circuit 30 if it was previously completed, and thereby activating the auto-injector 10. Such completion or breaking of a circuit has been discussed previously.

In further examples, the connector 45 may be coupled to a cap 12 of the auto-injector 10, wherein the cap 12 is detached from the auto-injector 10 by the connector 45 as the auto-injector 10 is removed from the device 100. In other examples, the connector 45 may be attached to a mechanism of the auto-injector 10, such as a safety catch or valve. Removal of the auto-injector 10 from the device 100 may cause the connector 45 to move the mechanism from a first position (in which the auto-injector 10 is non-activated) to a second position (in which the auto-injector 10 is activated). Following movement of the mechanism from the first position to the second position, continued removal of the auto-injector 10 from the device 100 causes the connector 45 to decouple from the auto-injector 10. This allows the auto-injector 10 to be completely removed from the device 100.

Figure 5A:
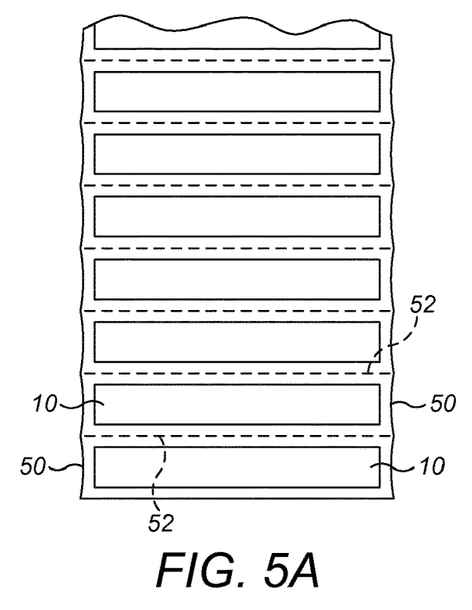
FIG. 5A is a front view of a plurality of blister packs, containing an auto-injector and suitable for use with embodiments of the present invention.
Figure 5B:
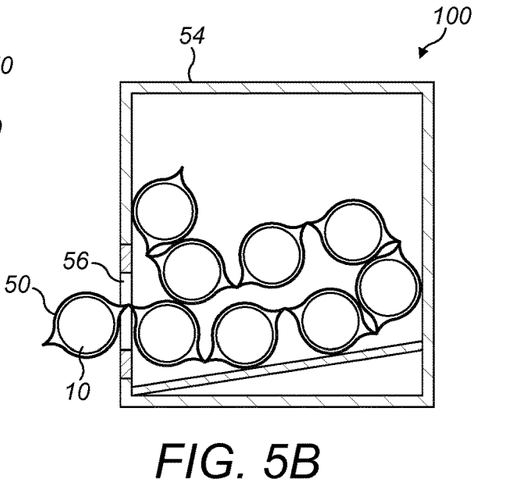
FIG. 5B is a box containing the plurality of blister packs of FIG. 5A.
Figure 5C:
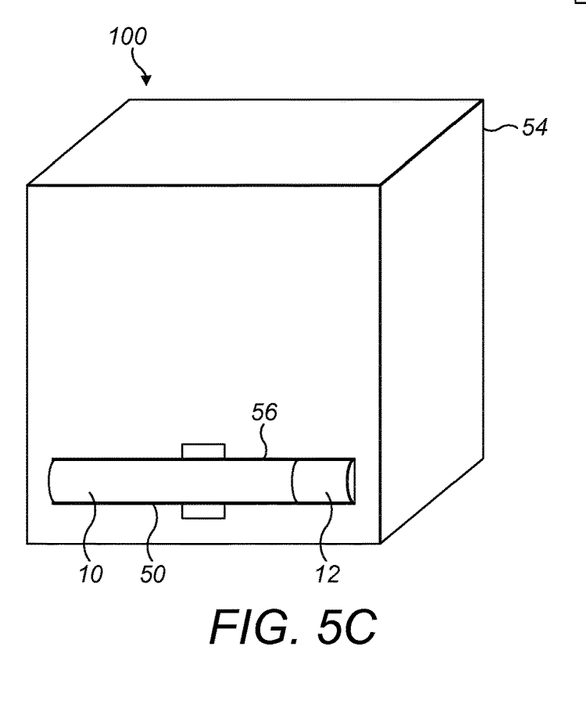
FIG. 5C is an isometric view of the box of FIG. 5B.

FIGS. 5A-C show a device 100 and auto-injectors 10.

FIG. 5A shows a plurality of blister packs 50. Each blister pack contains one auto-injector 10 sealed within. Sealing an auto-injector 10 within an individual blister pack 50 allows the sterility of the auto-injector 10 to be maintained up until the point of use.

FIG. 5A shows the plurality of blister packs 50 are coupled together, with individual blister packs 50 delimited by perforations 52. A single blister pack 50 may be separated from the remaining blister packs by tearing along the perforation 52. Alternatively, individual blister packs 50 may be entirely separate from each other (i.e. not coupled together).

FIG. 5B shows the plurality of blister packs 50 of FIG. 5A contained within a box or container 54 of the device 100. The blister packs 50 (and hence auto-injectors 10) may be arranged in the box in a variety of manners including behind one another or next to each other, in a horizontal or vertical direction, coiled (similar to FIG. 5B), or disorganised (as shown in FIG. 5B).

The device 100 comprises a dispenser 56 arranged to dispense an auto-injector 10 contained within a blister pack 50 within the box 54. FIG. 5B shows the dispenser 56 as an aperture through which a single auto-injector 10 can be removed from the box 54 at a time. FIG. 5C shows another view of the device 100 of FIG. 5C, showing the dispenser 56 and an auto-injector 10 being dispensed.

A blister pack 50 as shown in FIGS. 5A-C may comprise a connector 45 such as a tab coupled to the blister pack 50 and the auto-injector 10. The connector 45 is configured to decouple from the auto-injector 10 to activate the auto-injector 10. The connector operates as previously described with respect to FIG. 4.

FIG. 5C shows an isometric view of the device 100 of FIG. 5B. In this case the dispenser 56 is shown to be dimensioned such that no more than one auto-injector 10 can be removed from the box 54 at the same time. The dispenser 56 is thus configured to inhibit removal of two or more auto-injectors 10 from the device 100 simultaneously. If the plurality of blister packs 50 are coupled together as shown in FIG. 5A then removal of one blister pack 50 from box 54 via dispenser 56 will cause the next blister pack 50 to be pulled towards the dispenser 56 ready to be removed subsequently.

According to some examples, the device 100 is configured to activate an auto-injector 10 by at least partially opening a blister pack 50 containing the auto-injector 10. The device 100 may comprise an opening mechanism such as a sharp protrusion arranged to partially open or tear the blister pack 50 as the auto-injector 10 contained within the blister pack is removed from the device 100. Wherein the device 100 comprises a container 54 as shown in FIG. 5C, the opening mechanism may be comprised adjacent the dispenser 56.

According to some examples, the device 100 may comprise a locking mechanism. The locking mechanism may be movable between a locked state, in which removal of at least one auto-injector 10 from the device 100 is prevented, and an unlocked state, in which the at least one auto-injector 10 may be removed from the device 100. The locking mechanism may be moved from the locked state to the unlocked state by a key stored in or on the device 100. A user uses the key to move the locking mechanism from the locked state to the unlocked state and thus remove an auto-injector 10 from the device 100. The locking mechanism may comprise a mechanical or electronic lock.

The device 100 may comprise a plurality of locking mechanisms, each corresponding to a respective auto-injector 10, and a plurality of keys. Each key may correspond to a respective locking mechanism such that that particular key may move only that respective locking mechanism from the locked state to the unlocked state. Each key therefore only unlocks a particular auto-injector 10 from the device 100, allowing that auto-injector to be removed from the device 100. The locking mechanisms and keys act as an anti-tamper mechanism, so that specific auto-injectors 10 are only activated by specific removal from a specific locking mechanism. The device 100 may be configured to release a key in response to an authorised input, for example by input of an authorisation code into a circuit 30. The device 100 may comprise a plurality of boxes or containers 54 each comprising a respective locking mechanism, and each containing a respective auto-injector 10. A user may only be able to open a specific container 54 and remove a specific auto-injector 10 with a specific key.

Figure 6A:
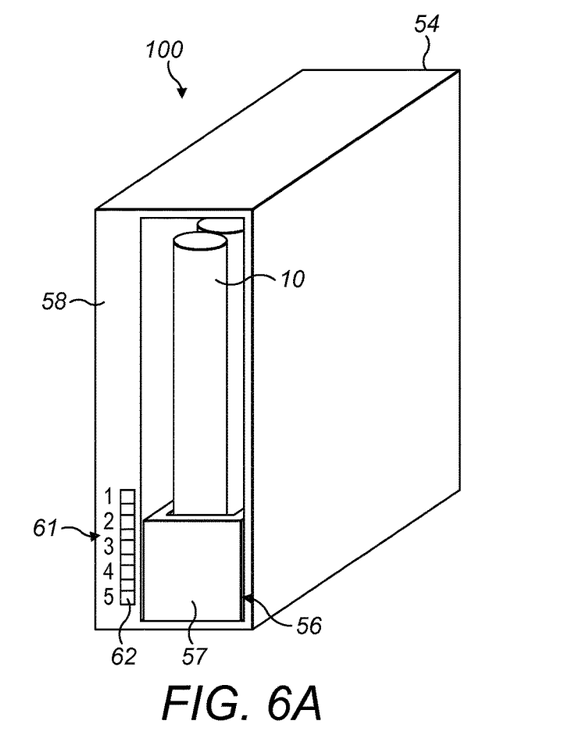
FIG. 6A is an isometric view of a device.
Figure 6B:
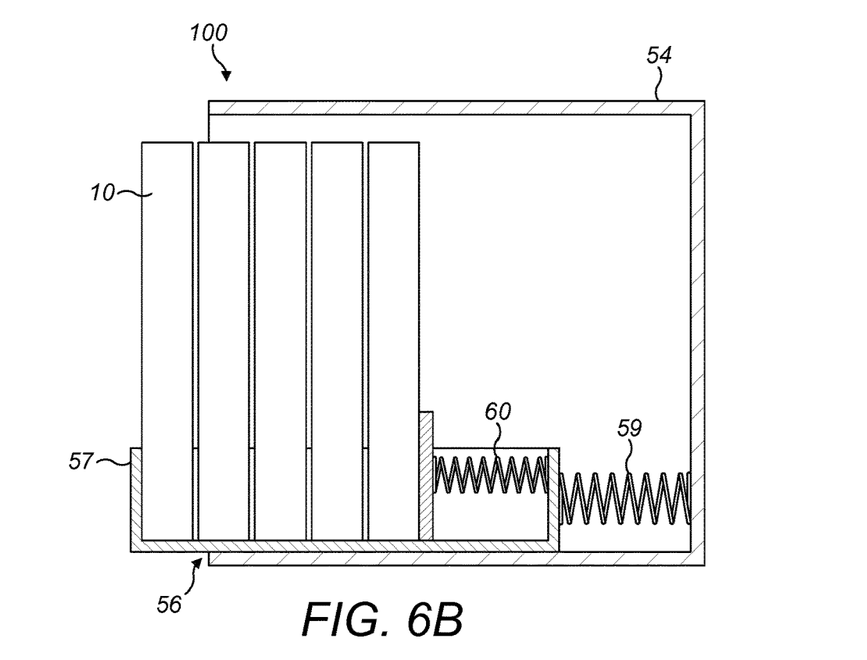
FIG. 6B is a cross-sectional view of the device of FIG. 6A.

FIG. 6A shows an example device 100. FIG. 6B show a cross-sectional view of the device 100 of FIG. 6B.

FIGS. 6A and 6B show the device 100 comprises a box 54 configured to contain an auto-injector 10. Similar to FIGS. 5B and 5C, the device 100 comprises a dispenser 56 arranged to dispense an auto-injector 10 contained within the box 54.

The dispenser 56 may be configured to inhibit removal of two or more auto-injectors 10 from the device 100 simultaneously. In other words, the dispenser 56 may be configured such that only one auto-injector 10 at a time can be removed from the device 100 by a user.

FIGS. 6A and 6B show the dispenser 56 comprises a drawer 57 arranged at a surface 58 of the box 54. The drawer 57 is moveable between an open position as shown in FIG. 6B and a closed position as shown in FIG. 6A.

When the drawer 57 is in the closed position, removal of an auto-injector 10 from the device 100 is prevented. When the drawer 57 is in the open position, an auto-injector 10 can be removed by a user from the device 100 via the drawer 57. As FIG. 6B shows, the left-most auto-injector 10 is ready to be removed by a user from the device 100.

Removal of the remaining auto-injectors 10 from the device 100 is inhibited by the drawer 57. The drawer 57 may only be allowed to move a certain distance that allows only a single auto-injector 10 to be presented to a user for removal. A first resilient member 59 (such as a spring) may be coupled to the drawer 57 and to the box 54 to bias the drawer from the open position to the closed position.

The drawer 57 may further comprise a second resilient member 60 configured to apply a biasing force to a plurality of auto-injectors 10 contained within the drawer 57 such that if an auto-injector 10 is removed from the drawer 57, another auto-injector 10 of the plurality of auto-injectors 10 will be pushed to the front of the drawer ready for removal by a user.

The device 100 may comprise a display 61 indicating the number of auto-injectors 10 stored within the box 54. FIG. 6A shows the display 61 is an electronic display comprising a plurality of LEDs 62, but an electronic display comprising an LCD may be used instead. The display may be updated based upon an electronic system comprising a photo sensor monitoring the number of auto-injectors 10 stored in the box 54. The display 61 may alternatively be a mechanical display, wherein the display is updated based upon a mechanical counter wheel monitoring the number of auto-injectors 10 stored in the box 54. Alternatively, or in addition, the box 54 may comprise a window (not shown) for a user to see the number of auto-injectors 10 contained within.

Each of the auto-injectors 10 may be activated in response to removal from the drawer 57. In some examples, the drawer 57 may be configured to detach a part of an auto-injector 10 as it is removed from the drawer 57. For example, the drawer 57 may be configured to detach a cap 12 of an auto-injector 10 as it is removed from the drawer 57. The drawer 57 may comprise coupling means arranged to couple to the cap 12 of an auto-injector 10. The cap 12 may remain in the drawer 57 after removal of the auto-injector 10.

Figure 7A:
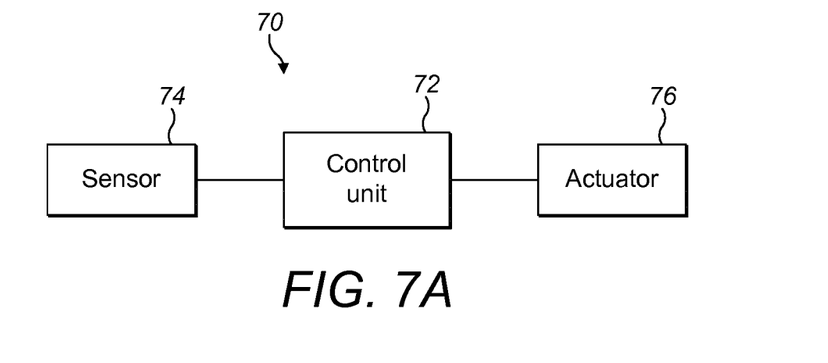
FIG. 7A is a schematic diagram of a circuit within a device.

FIG. 7A is a schematic diagram of a circuit 70 that may be comprised within a device 100. The circuit 70 comprises a control unit 72, a sensor 74 and an actuator 76. The sensor 74 and actuator 76 are electrically coupled to the control unit 72. The control unit 72 can control operation of the sensor 74 and actuator 76.

The sensor 74 is configured to sense a whether or not an auto-injector 10 has been activated, and to send a corresponding signal to the control unit 72 indicating whether or not the auto-injector 10 has been activated. The sensor 74 may be a mechanical sensor such as a switch that can only be activated by particular configurations of the auto-injector 10, or an electronic sensor such as a light sensor, RFID sensor, or Hall sensor. The control unit 72 is configured to determine whether the auto-injector 10 has been activated based upon the signal received from the sensor 74.

The actuator 76 is an electrical actuator, such as a motor or solenoid, which is controlled by the control unit 72. The actuator 76 is moveable between a first position and a second position. The actuator 76 is arranged in the device 100 such that in the first position an auto-injector 10 being sensed by the sensor 74 can be stored in the device 100, while in the second position the same auto-injector 10 is inhibited from being stored in the device 100. The control unit 72 can send a signal to the actuator 76 to cause the actuator to move from the first position to the second position, or vice versa.

In response to determining that the auto-injector 10 has been activated based upon the signal received from the sensor 74, the control unit 72 is configured to send a signal to the actuator 76 to move it from the first position to the second position. As a result, the activated auto-injector 10 sensed by the sensor 74 is inhibited from being stored in the device 100. This has the advantage of preventing a user from trying to re-store an activated auto-injector 10 (that has already been removed from the device 100) back in the device 100. The result is that a user is encouraged to use that particular auto-injector 10 before removing another one.

Figure 7B:
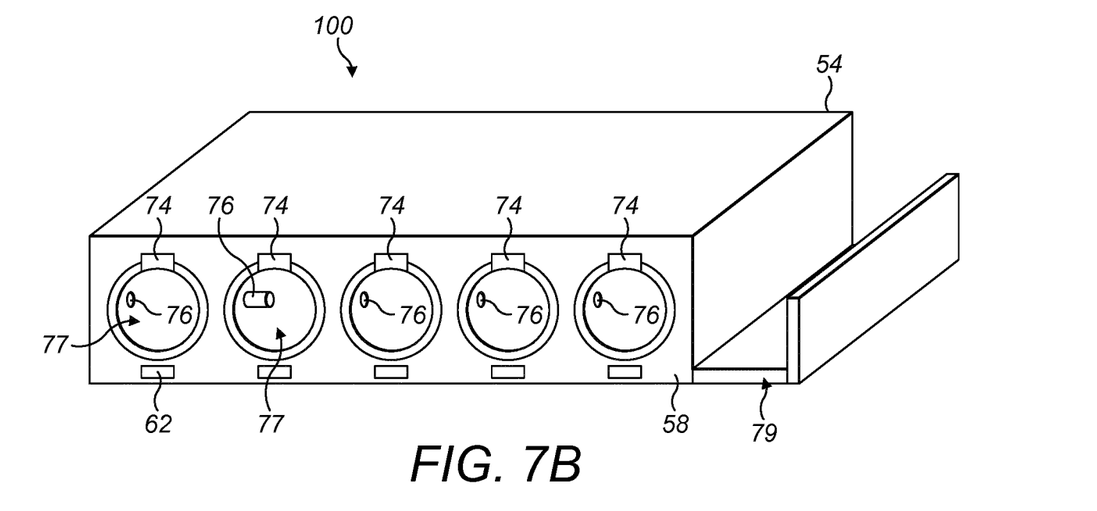
FIG. 7B is an isometric view of a device containing the circuit of FIG. 7A.

FIG. 7B shows an embodiment of the present invention. The device 100 comprises a box 54 for storing a plurality of auto-injectors 10 (not shown). In this embodiment, the device 100 comprises a plurality of apertures 77 arranged at a surface 58 of the box 54. Each aperture 77 is configured to store a respective auto-injector 10. In the example shown in FIG. 7B, the device 100 has five apertures 7 and so can store five auto-injectors 10, however the present disclosure is not limited to this number and a larger or smaller number of auto-injectors 10 may be stored in the device 100.

The device 100 of FIG. 7B may contain a circuit 70 as described with reference to FIG. 7A. FIG. 7B shows a sensor 74 arranged proximal to each aperture 77. Each sensor 74 is electrically coupled to the control unit 72 (not shown). Each sensor 74 is configured to sense whether or not an auto-injector 10 brought into close proximity of the corresponding aperture 77 has been activated. The device 100 also comprises a plurality of actuators 76 each electrically coupled to the control unit 72. Each aperture 77 has an actuator 76 arranged proximal to each aperture 77. For each actuator 76 arranged proximal to a respective aperture 77, when the actuator 76 is in a first position an auto-injector 10 can be stored in the respective aperture 77, while when the actuator 76 is in a second position an auto-injector 10 is inhibited from being stored in the respective aperture 77. The left-most actuator 76 is in the first position, while the first actuator 76 on the right of the left-most actuator is in the second position.

Operation of the device 100 is shown in FIG. 7B. A non-activated auto-injector 10 is stored in an aperture 77 of the device 100. The auto-injector 10 is removed from the device 100 by a user withdrawing the auto-injector 10 from the aperture 77. In response to removal of the auto-injector 10 from the device 100, the device 100 automatically activates the auto-injector 10. A user attempts to store the activated auto-injector 10 in the same aperture 77 (or perhaps another aperture 77) of the device 100. The user brings the auto-injector 10 into proximity of an aperture 77, thereby bringing the auto-injector 10 into proximity of the sensor 74 arranged proximal to each aperture 77. The sensor 74 senses that the auto-injector 10 has been activated and sends a corresponding signal to the control unit 72. In response to the control unit 72 determining from the signal that the auto-injector 10 has been activated, the control unit 72 sends a signal to the actuator 76 proximal to each aperture 77 to move it from a first position to a second position. While the actuator 76 is in the second position, the auto-injector 10 is inhibited from being stored in the aperture 77.

FIG. 7B shows that the device 100 may further comprise a shelf 79 configured to store an activated auto-injector 10. The shelf 79 is arranged at a surface of the box 54. A user may remove an auto-injector 10 from the device 100, thereby activating the auto-injector 10, but may not want to use the auto-injector 10 until later. The user may be prevented from re-storing the activated auto-injector 10 in the device 100, as described earlier. The shelf 79 therefore provides a convenient location for the user to store the activated auto-injector 10 until it is ready to be used. The user is encouraged to use the activated auto-injector 10 stored on the shelf first, before activating a new auto-injector 10 stored elsewhere in the device 100.

The present disclosure also relates to a system comprising a device 100 and an auto-injector 10, including, but not limited to, those previously described. The auto-injector 10 of the system is configured to be activated by the device 100 in response to being removed from the device 100.

Figure 8:
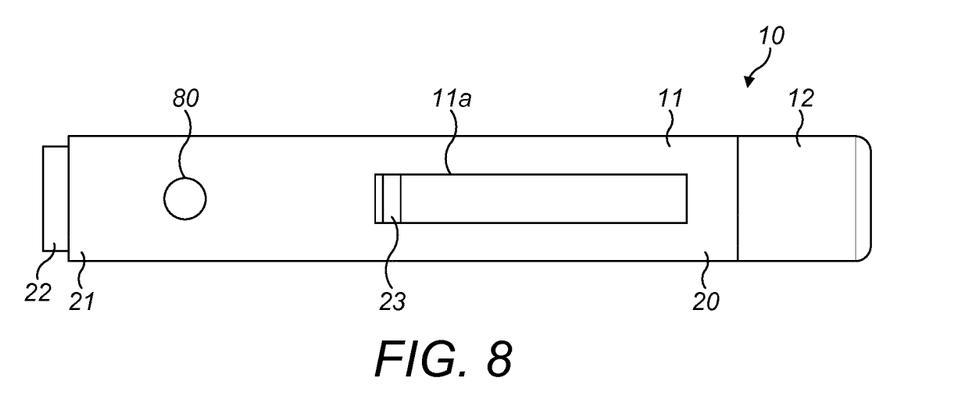
FIG. 8 is a side view of an auto-injector.

FIG. 8 shows an auto-injector 10. The system may comprise an activation indicator 80, wherein the activation indicator 80 is configured to indicate to a user that the auto-injector 10 is activated. FIG. 8 shows the auto-injector 10 comprises the activation indicator 80. In this case, the activation indicator 80 comprises an L.E.D., but it may additionally or alternatively comprise a display or a speaker. In other embodiments the device 100 may comprise the activation indicator 80.

Figure 9:
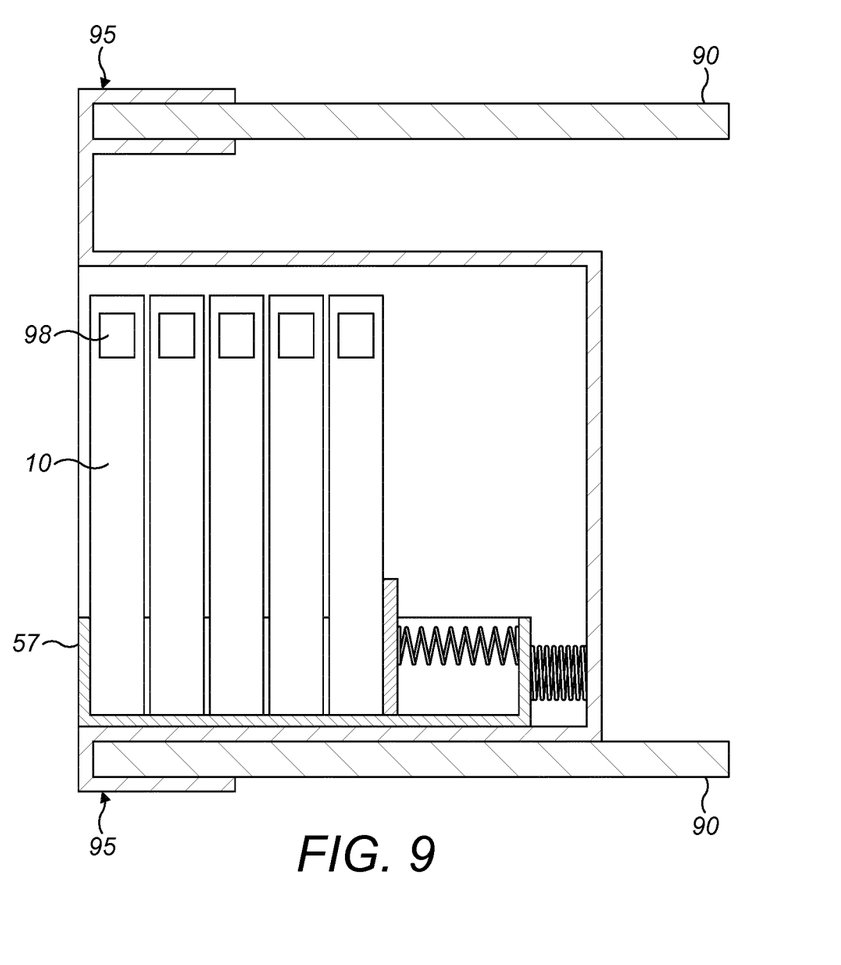
FIG. 9 is a cross-sectional view of an auto-injector storage device.

FIG. 9 is a cross-sectional view of an auto-injector storage device 100. The device 100 is similar to the device 100 shown in FIGS. 6A and 6B. The device 100 may comprise an attachment mechanism 95 arranged to couple the box 54 to one or more racks 90 of a refrigerator. The refrigerator is configured to refrigerate an auto-injector 10 stored in the device 100 when the device 100 is coupled to the rack 90. In the example shown in FIG. 9, the refrigerator comprises an upper and lower rack 90. The attachment mechanism 95 comprises a recess configured to receive at least part of the racks 90.

The system of FIG. 9 further comprises a temperature indicator 98 configured to indicate a temperature of the auto-injector 10 to a user, wherein the temperature indicator 98 is activated upon removal of the auto-injector 10 from the device 100.

It is often necessary to refrigerate medicaments below room temperature to slow degeneration of the medicaments. However, it may also be necessary or preferred to raise the temperature of the medicaments to a temperature above the refrigerated temperature prior to an injection. For example, it may be required or preferred to allow the medicament to reach room temperature prior to injection.

The temperature indicator 98 of FIG. 9 is entirely comprised in the auto-injector 10, however the temperature indicator 98 may alternatively be comprised in any part of the system. The temperature indicator 98 may comprise a thermometer coupled to an LED (not shown). When the refrigerated auto-injector 10 is removed from the device 100, the temperature indicator 98 is activated. The temperature indicator 98 monitors a temperature of the auto-injector 10, such as a temperature of the medicament contained within the auto-injector 10. The temperature may be monitored using the thermometer. The temperature indicator 98 indicates the temperature to a user. The temperature may be continuously monitored and indicated to a user. Alternatively, the temperature may be indicated to a user once a threshold temperature has been reached, such as a temperature suitable for injection. Reaching the threshold temperature may be indicated to the user by the LED switching on (or off, or blinking).

Although claims have been formulated in this application to particular combinations of features, it should be understood that the scope of the disclosure also includes any novel features or any novel combinations of features disclosed herein either explicitly or implicitly or any generalisation thereof, whether or not it relates to the same disclosure as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although several embodiments have been shown and described, it would be appreciated by those skilled in the art that changes may be made in these embodiments without departing from the principles of the disclosure, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')₂ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A storage device for storing a plurality of auto-injectors, the storage device configured to activate an auto-injector as the auto-injector is removed from the storage device by at least partially opening a blister pack containing the auto-injector as the auto-injector is removed from the storage device.

2. The storage device of claim 1, wherein the storage device is configured to activate the auto-injector by breaking or completing an electrical circuit of the auto-injector.

3. The storage device of claim 1, wherein the storage device is configured to activate the auto-injector by detaching a part of the auto-injector.

4. The storage device of claim 1, comprising a connector coupled to the auto-injector, wherein the connector is configured to decouple from the auto-injector to activate the auto-injector.

5. The storage device of claim 4, wherein the storage device comprises the blister pack configured to contain the auto-injector, wherein the connector is coupled to the blister pack and the auto-injector and is configured to decouple from the auto-injector to activate the auto-injector.

6. The storage device of claim 1, wherein the storage device comprises a box configured to contain the auto-injector, wherein the storage device comprises a dispenser arranged to dispense an auto-injector contained within the box, and wherein the dispenser is configured to inhibit removal of two or more auto-injectors from the storage device simultaneously.

7. The storage device of claim 1, wherein the plurality of auto-injectors contain a medicament.

8. The storage device of claim 7, further comprising an activation indicator, wherein the activation indicator is configured to indicate to a user that the auto-injector is activated.

9. The storage device of claim 7, wherein the storage device comprises a temperature indicator configured to indicate a temperature of the auto-injector to a user, wherein the temperature indicator is activated upon removal of the auto-injector from the storage device.

10. The storage device of claim 1, wherein the storage device comprises a protrusion configured to at least partially open the blister pack as the blister pack is removed from the storage device.

11. A method for activating an auto-injector, the method comprising:
  removing the auto-injector from a storage device;
  wherein the storage device is configured to store a plurality of auto-injectors;
  wherein the removing causes activating of the auto-injector by at least partially opening a blister pack containing the auto-injector as the auto-injector is removed from the storage device; and,
  wherein the activating comprises changing the auto-injector from a state preventing discharging of a dose of medicament to a state permitting discharging of the dose of medicament.

12. The method of claim 11, wherein the activating comprises breaking or completing an electrical circuit of the auto-injector.

13. The storage device of claim 11, wherein the storage device is configured to activate the auto-injector by detaching a part of the auto-injector.

14. The method of claim 11, wherein the storage device comprises a protrusion configured to at least partially open the blister pack as the blister pack is removed from the storage device.

15. A storage device for storing a plurality of auto-injectors, the storage device configured to activate an auto-injector as the auto-injector is removed from the storage device by decoupling a connector from the auto-injector as the auto-injector is removed from the storage device,
  wherein the connector is coupled to the auto-injector and a blister pack configured to contain the auto-injector, wherein the connector is configured to decouple from the auto-injector to activate the auto-injector,
  wherein the storage device comprises the blister pack.

16. A storage device for storing a plurality of auto-injectors, the storage device configured to activate an auto-injector as the auto-injector is removed from the storage device by physically modifying the auto-injector as the auto-injector is removed from the storage device,
  wherein the storage device comprises a box configured to contain the auto-injector,
  wherein the storage device comprises a dispenser arranged to dispense an auto-injector contained within the box, wherein the dispenser is configured to inhibit removal of two or more auto-injectors from the storage device simultaneously,
  wherein the dispenser comprises a drawer moveable between an open position and a closed position, and
  wherein an auto-injector is removable from the storage device via the drawer when the drawer is in the open position.

17. The storage device of claim 16, wherein the storage device is configured to inhibit subsequent storage of the auto-injector in the storage device after the auto-injector has been previously removed from the storage device and activated.

18. The storage device of claim 17, wherein the storage device is configured to activate the auto-injector as the auto-injector is removed from the storage device by physically detaching a cap from the auto-injector as the auto-injector is removed from the storage device.

19. The storage device of claim 17, wherein the storage device is configured to activate the auto-injector by breaking or completing an electrical circuit of the auto-injector.

20. The storage device of claim 17, wherein the storage device is configured to activate the auto-injector by detaching a part of the auto-injector.

* * * * *

UNITED STATES PATENT AND TRADEMARK OFFICE
CERTIFICATE OF CORRECTION

PATENT NO. : 11,147,911 B2
APPLICATION NO. : 16/609959
DATED : October 19, 2021
INVENTOR(S) : Wendland et al.

Page 1 of 1

It is certified that error appears in the above-identified patent and that said Letters Patent is hereby corrected as shown below:

In the Claims

Column 20, Line 4, Claim 13, delete "storage device" and insert -- method --

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*